(12) United States Patent
Staudenmeier

(10) Patent No.: US 6,547,820 B1
(45) Date of Patent: Apr. 15, 2003

(54) HIGH PROFILE FABRIC GRAFT FOR ARTERIOVENOUS ACCESS

(75) Inventor: Marianne W. Staudenmeier, North Haledon, NJ (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/678,865

(22) Filed: Oct. 3, 2000

(51) Int. Cl.[7] .................................................. A61F 2/06
(52) U.S. Cl. ...................... 623/1.49; 623/1.5; 623/1.51; 623/1.52; 264/103
(58) Field of Search .............................. 623/1.49, 1.5, 623/1.51, 1.52, 1.53, 1.54; 264/103; 66/169

(56) References Cited

U.S. PATENT DOCUMENTS

| | | | |
|---|---|---|---|
| 2,652,701 A | 9/1953 | Longhurst | 65/13 |
| 3,581,953 A | 6/1971 | Donoghue | 222/207 |
| 3,878,565 A | 4/1975 | Sauvage | |
| 4,047,252 A * | 9/1977 | Liebig et al. | 623/1.5 |
| 4,193,137 A * | 3/1980 | Heck | 623/1.5 |
| 4,652,263 A * | 3/1987 | Herweck et al. | 623/1.51 |
| 4,892,539 A * | 1/1990 | Koch | 623/1.51 |
| 5,178,630 A | 1/1993 | Schmitt | |
| 5,370,682 A | 12/1994 | Schmitt | |
| 5,383,925 A | 1/1995 | Schmitt | |
| 5,405,030 A | 4/1995 | Frazier | 215/6 |
| 5,456,711 A * | 10/1995 | Hudson | 623/1.5 |
| 5,509,931 A | 4/1996 | Schmitt | |
| 5,700,287 A | 12/1997 | Myers et al. | |
| 5,711,452 A | 1/1998 | Chaffin | 220/715 |
| 5,716,395 A | 2/1998 | Myer et al. | |
| 5,732,572 A * | 3/1998 | Litton | 623/1.5 |
| 5,741,332 A * | 4/1998 | Schmitt | 623/1.53 |
| 5,753,289 A | 5/1998 | Ness | 426/394 |
| 5,840,240 A | 11/1998 | Stenoien et al. | |
| 5,866,217 A | 2/1999 | Stenoien et al. | |
| 5,910,168 A | 6/1999 | Myers et al. | |
| 5,911,753 A | 6/1999 | Schmitt | |
| 5,913,894 A | 6/1999 | Schmitt | |
| 6,090,137 A * | 7/2000 | Schmitt | 623/1.44 |
| 6,221,099 B1 * | 4/2001 | Andersen et al. | 623/1.15 |

FOREIGN PATENT DOCUMENTS

| | | |
|---|---|---|
| EP | 0327903 A1 | 8/1989 |
| WO | WO 92/03107 | 3/1992 |

* cited by examiner

Primary Examiner—David H. Willse
Assistant Examiner—Suzette J. Jackson
(74) Attorney, Agent, or Firm—Hoffmann & Baron, LLP

(57) ABSTRACT

A fabric graft having a high external velour profile is provided. The textile graft may be woven or knitted to form a tubular prosthesis. The high external velour profile is provided by outwardly extending loops ranging from about 1 mm to about 5 mm in length. The fabric graft is self-sealing to minimize bleeding after puncture by a dialysis needle.

26 Claims, 4 Drawing Sheets

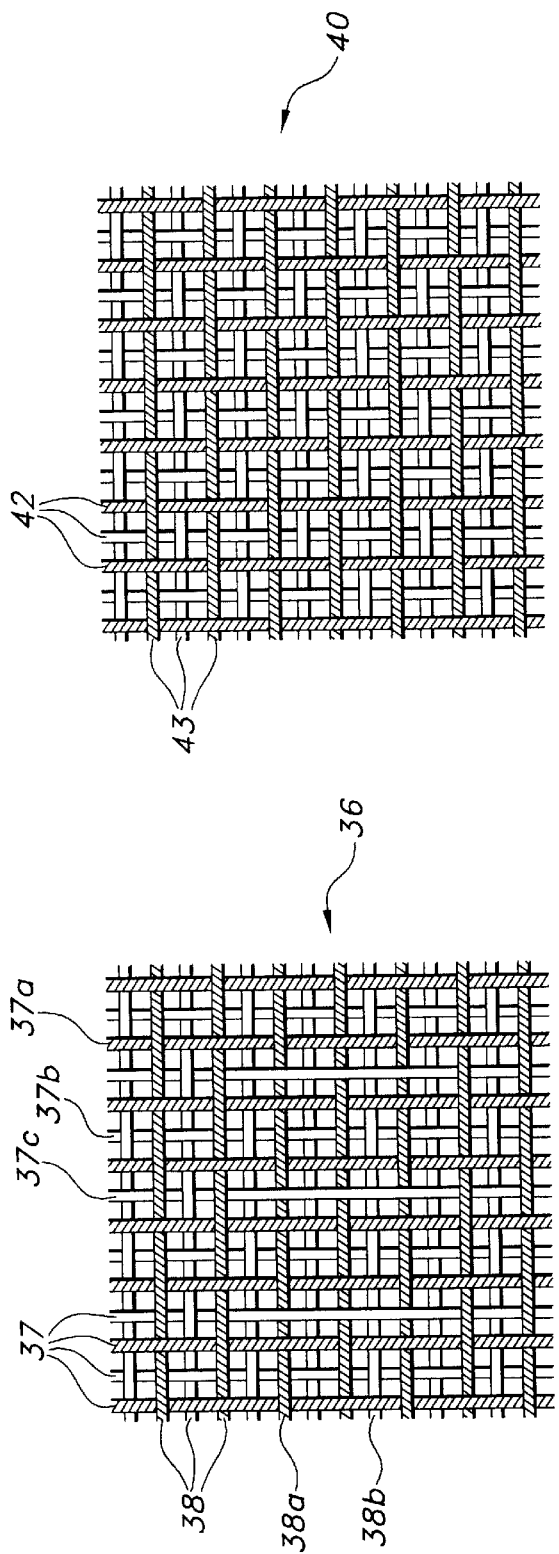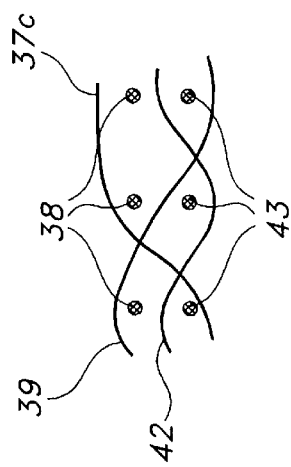
FIG 7
FIG 8
FIG 6

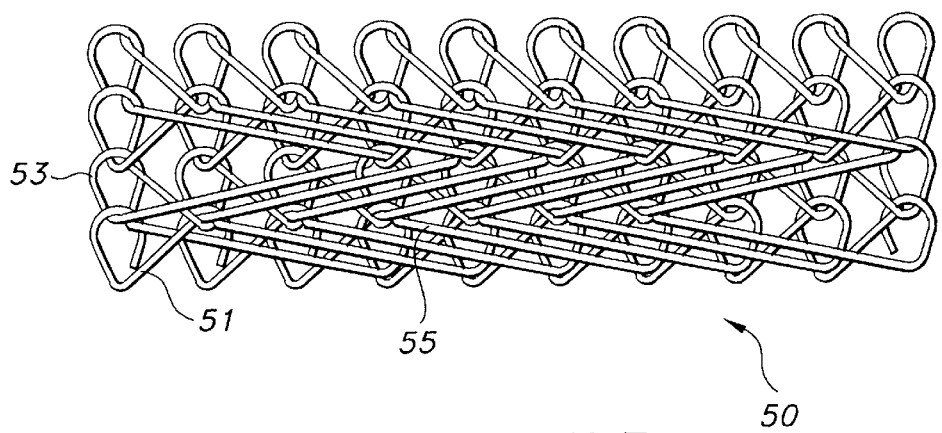
FIG 11
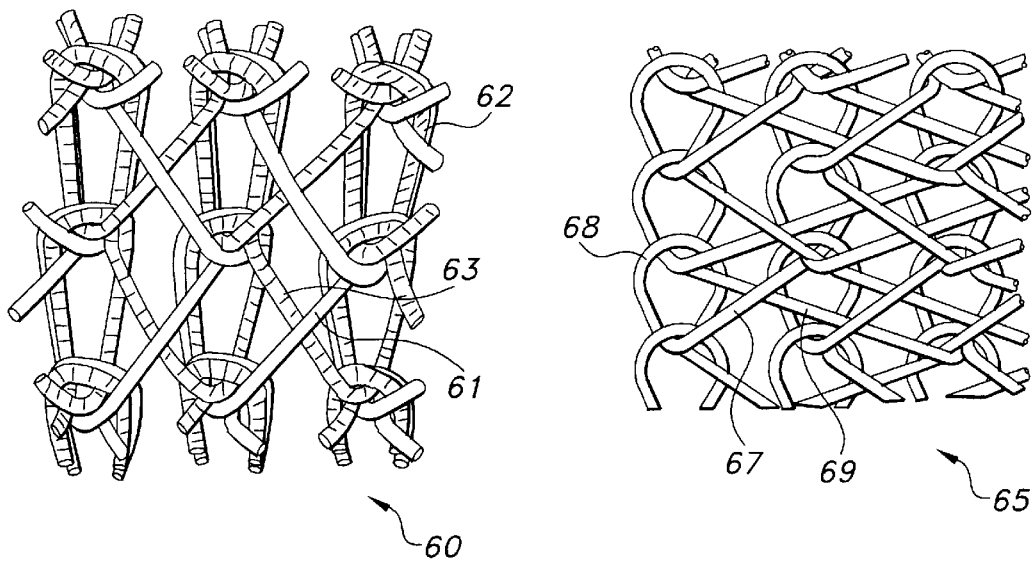
FIG 12
FIG 13

HIGH PROFILE FABRIC GRAFT FOR ARTERIOVENOUS ACCESS

FIELD OF THE INVENTION

This invention relates to a fabric graft for use with dialysis treatment of blood in general, and more particularly to a high profile graft for arteriovenous access during dialysis treatment.

BACKGROUND OF THE INVENTION

A healthy kidney removes toxic wastes and excess water from the blood. With partial or chronic renal disease, however, the kidneys progressively stop performing these essential functions. Dialysis treatment is often required to remove toxins and excess water from the blood of a patient.

Hemodialysis therapy is an extracorporeal process which removes toxins and water from a patient's blood. A hemodialysis machine pumps blood from the patient, through a dialyzer, and then back to the patient. The dialyzer removes the toxins and water from the blood by a membrane diffusion principle. Typically, a patient with chronic kidney disease requires hemodialysis three times per week for 3–6 hours per session. Removing blood from the body requires a vascular access to the patient's blood system. This vascular access can be accomplished by surgically modifying the patient's own blood vessels or attaching an artificial device to the blood vessels. If the vascular access site is entirely beneath the skin, the skin and the vascular site is punctured by a needle for access.

Arteriovenous (AV) shunts have been used in the past to provide vascular access. The AV shunt employs a tube sutured to an artery. The tube is tunneled subcutaneously and exited through the skin where it connects to another tube. This second tube penetrates back through the skin and is sutured to a vein. During hemodialysis, the arterial tube connects to an input line of a dialysis machine, and the venous tube connects to the machine's return line.

Because a portion of the tube remains outside the skin, patients typically suffer a relatively high rate of infection. Other problems associated with the AV shunt include skin disfigurement and frequent clotting.

Problems associated with these transcutaneous shunts led to the development of a native arteriovenous (AV) fistula which remains subcutaneous post-surgery and avoids to some extent the infection problem associated with transcutaneous devices. The AV fistula is a surgical construct subcutaneously connecting a patient's major artery to a major vein at a convenient location, such as in the arm. With this resulting new blood flow path, most blood will bypass the high flow resistance of the downstream capillary bed, thereby producing a dramatic increase in the blood flow rate through the fistula. Two fistula needles, connected to tubing leading to and from the hemodialysis machine, are used to puncture the skin to gain access to the arterialized vein. Blood is withdrawn from the arterial side of the vein, passes through the dialysis machine, where it is cleansed, and returns to the venous side of the access.

The AV fistula, however, requires four to eight weeks to mature and cannot be used for dialysis access during this time period. The AV fistula matures by thickening of the fistula vein due to increased arterial pressure and arterial flow thereat. After the fistula vein matures or arterializes it becomes feasible to repeatedly puncture the AV fistula vein. The arterialized vein can then be punctured repeatedly, and the high blood flow permits hemodialysis treatment thereat. The AV fistula technique, however, cannot be used on many dialysis patients because the patients who are elderly, diabetic or suffer from arterial disease generally lack usable peripheral veins.

AV grafts made from synthetic materials, such as polytetrafluoroethylene (PTFE), polyurethane or silicone, have been used as alternatives to arteriovenous shunts and fistulas. Implanted in a surgical procedure, the AV graft connects an artery to a vein, forming a bypass which can be punctured by needle sets in the same way a normal AV fistula is accessed.

The AV grafts are commonly used when the patient's own blood vessels are too small for fistula construction. These grafts, however, typically require about two to four weeks for adequate healing and sufficient tissue growth to stabilize the graft. During this time period the AV graft is generally unavailable for dialysis access.

An AV graft made from conventional PTFE or ePTFE extruded tubes have the disadvantage in that the graft is typically not self-sealing after puncture by a dialysis needle. Digital pressure is often applied near the puncture site for several minutes to prevent bleeding through the puncture site. A polyurethane graft is known to be somewhat unstable in the body. A silicone material generally has greater flexibility than a PTFE material. An AV graft made from silicone has better self-sealing characteristics as compared to an AV graft made from PTFE because of the increased flexibility of the silicone material. Such silicone AV grafts, however, are often stiff and uncomfortable as compared to an AV graft made from PTFE.

There is a need for a self-sealing AV graft that does not have the disadvantages of the ePTFE, polyurethane or silicone AV grafts. In particular, there is a need for a self-sealing AV graft that does not require extended periods of time for healing and tissue growth prior to use in hemodialysis.

SUMMARY OF THE INVENTION

The present invention is an AV graft made from synthetic fibers or yarns and having a high external profile to facilitate tissue ingrowth and to provide self-sealing of the graft after puncture by a dialysis needle, or the like. The AV graft includes elastic synthetic fibers to provide a self-sealing mechanism after puncture.

The AV graft of the present invention includes a woven or knitted pattern of yarns. The woven or knitted pattern provides for self-sealing after puncture. The AV graft has a high external profile to promote tissue ingrowth after implantation and to further provide self-sealing of the graft after puncture.

In one aspect the high profile AV graft is a woven graft having a first fabric layer of a plain or twill pattern to provide a smooth interior surface of the graft. A second fabric layer having raised loops is provided to give the AV graft a high external profile. The second fabric layer has raised loops of fabric extending outwardly from the outer surface to provide a raised or velour texture.

In a another aspect, the present invention includes a knitted pattern of yarns. A first fabric layer is provided with a close-knit pattern having a smooth inner surface. A second knit pattern of a second fabric layer has external loops that can be raised from the surface to provide a velour-like surface.

The fabric loops extending from the outer surface of the AV graft extends from about 1 to about 5 mm in length.

BRIEF DESCRIPTION OF THE DRAWINGS

FIG. 6 is a perspective view of a weaving pattern for the exterior portion of the high profile fabric graft of the present invention.

FIG. 7 is a perspective view of a weaving pattern for the interior portion of the high profile fabric graft of the present invention.

FIG. 8 is a partial cross-sectional view of weaving patterns having interlacing yarns between the exterior and the interior portions of the graft wall.

FIG. 11 is a perspective view of a knitting pattern for the exterior portion of the high profile fabric graft of the present invention.

FIG. 12 is a perspective view of a knitting pattern for the interior portion of the high profile fabric graft of the present invention.

FIG. 13 is a perspective view of an alternate knitting pattern for the interior portion of the high profile fabric graft of the present invention.

DETAILED DESCRIPTION OF THE INVENTION

The present invention addresses the problems associated with prior art AV grafts. The vascular graft of the present invention overcomes the disadvantages of presently available AV grafts by providing a vascular graft that is substantially self-sealing-without having the disadvantage of thick polymeric tubing. Furthermore, the AV graft of the present invention has a high profile exterior surface to facilitate tissue growth or stabilization. The combination of the self-sealing feature and high profile exterior surface of the present invention permits dialysis access to the AV graft without having to wait for two to four weeks for graft stabilization. The AV graft of the present invention is sufficiently stabilized for dialysis access within one week or less after implantation.

The high profile exterior surface also forms an interspatial volume about the AV graft. This interspatial volume is in conformity to the proximal intervascular region to fill any voids between the AV graft and the intervascular region resulting from implanting or tunneling of the AV graft into the hypodermic region between the artery and the vein used for the bypass.

Figure 1:
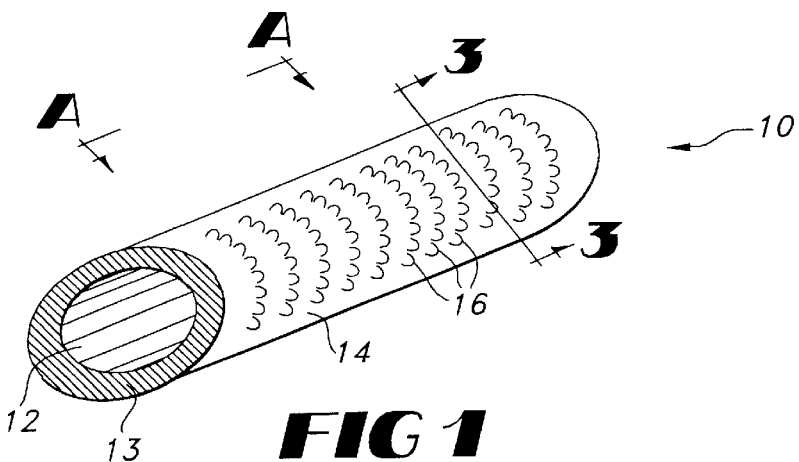
FIG. 1 is a perspective view of a high profile fabric graft of the present invention having an external profile extending in a longitudinal or warp direction.

FIG. 1 is a perspective view of vascular graft 10 of the present invention. Graft 10 includes a tubular wall 13 defined by a smooth inner surface 12 and external raised fabric velour surface 14. The velour surface 14 has a multiplicity of outward extending raised loops 16. Raised loops 16 extend circumferentially along the velour surface 14. A circumferential direction is also referred to as a warp direction herein.

Figure 2:
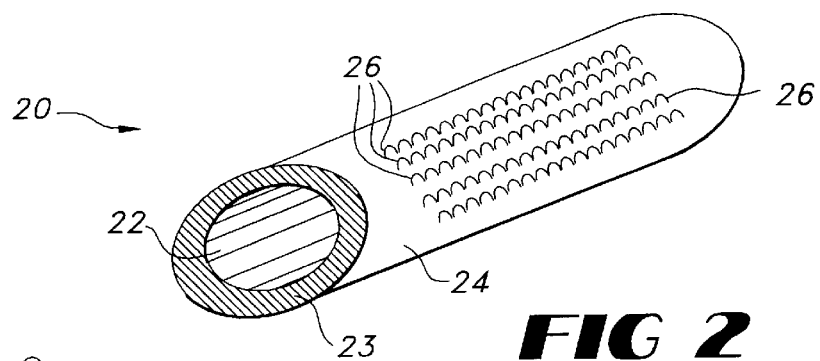
FIG. 2 is a perspective view of a second embodiment of a high profile fabric graft of the present invention having an external profile extending in a circumferential or fill direction.

FIG. 2 a perspective view of vascular graft 20 of the present invention. Graft 20 includes a tubular wall 23 defined by a smooth inner surface 22 and external raised fabric velour surface 24 of graft 20. The velour surface 24 of graft 20 also has a multiplicity of outward extending raised loops 26. As depicted in FIG. 2, raised loops 26 extend in a longitudinal or fill direction along the velour surface 24.

Figure 3:
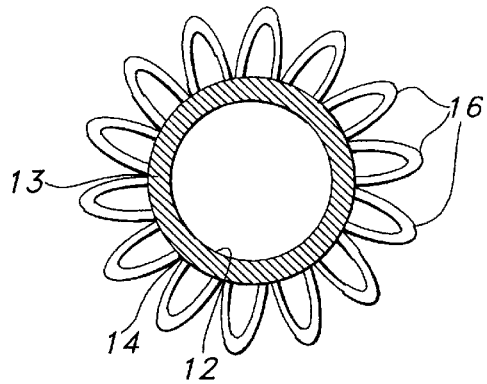
FIG. 3 is a cross-sectional view of the fabric graft of FIG. 1 taken along the 3—3 axis.
Figure 4:
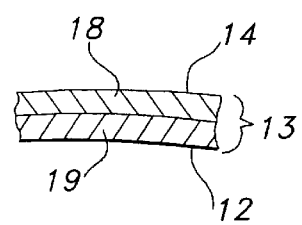
FIG. 4 is a partial cross-sectional view of the tubular wall of the high profile fabric graft of the present invention depicting an interior and an exterior portion of the wall.
Figure 5:
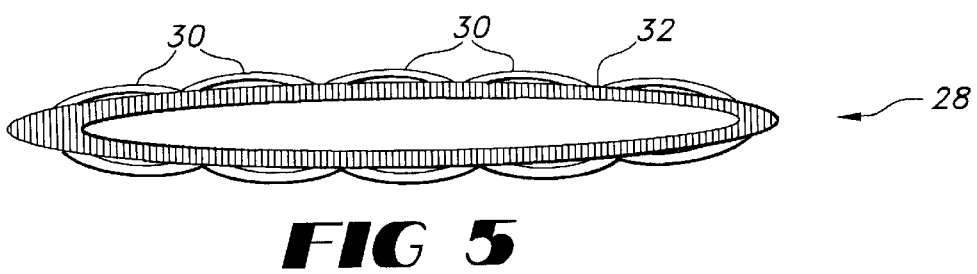
FIG. 5 is a cross-sectional view of a flat-woven or a flat-knitted fabric graft of the present invention.

FIG. 3 is a cross-sectional view of graft 10 taken along the 3—3 axis. Raised loops 16 outwardly extend in a radial fashion from velour surface 14. Graft 10 is depicted as a generally circular tube in FIGS. 1 through 3. In one aspect of the present invention graft 28 is generally flat in shape as depicted in FIG. 4 after initial formation of the graft. This generally flat tubular graft 28 can be subsequently processed as described herein to form a tubular vascular graft having a generally circular shape, such as graft 10. Loops 30 of flat-tubular graft 28 are proximal to outer surface 32 and are also in a general flat shape. Loops 30 can be subsequently raised outwardly from outer surface 32 to form raised loops, such as raised loops 16 or 26.

The degree or length which the raised loops 16 or 26 extend from the velour surface is an important aspect of the present invention. The raised loops 16 or 26 not only provide access for tissue ingrowth, but also have resiliency to return to their outwardly projecting shape after a disturbance or deformation from their original position. As used herein, the term "resiliency" and its variants refer to the ability of a material to resume its original shape or quiescent state after being deformed, such as being bent, stretched, compressed or the like. For example, when graft 10 is accessed by a dialysis needle (not shown) some of the raised loops 16 will be displaced from a quiescent state to an altered state by the needle. When the needle is removed, the raised loops 16 have resiliency to substantially return to their undisturbed or quiescent state. When the raised loops 16 are deformed, they return to a position that represents, but not limited to, from 50 to 100 percent of the position of the quiescent state.

The resiliency of raised loops 16 provide, in part, a self-sealing mechanism after a puncture of graft 10. Desirably, loops that outwardly project from about 1 mm to about 5mm from the exterior surface are useful with the present invention. Loops that extend outwardly less than 0.5 mm do not provide adequate resiliency and area for tissue ingrowth to be useful as an AV access graft in accordance with the present invention. For example, a time period of about two to four weeks would be required after a low profile, i.e., less than 0.5 mm of loop length, graft is surgically implanted before it an be used for dialysis access.

The high profile AV access graft of the present invention is a textile graft. Desirably, the textile graft is woven or a knitted fabric graft. Additionally, as depicted in FIG. 4, the tubular wall 13 of graft 10 includes an exterior layer 18 and an interior layer 19. Both of these layers are textile layers of synthetic yarns. These layers have elastic synthetic fibers that provide the AV access graft of the present invention with a self-sealing mechanism after puncture by a dialysis needle (not shown). As used herein, the term "elastic" and its variants refer to the ability of a material to resume its quiescent shape after being stretched or compressed to an altered state. Elastic fibers include, but are not limited to polyester fibers. Yarns made from crimped polyester containing fibers can be stretched to a considerable degree, such as 105 to 155 percent of their quiescent length, without breaking and further substantially returning to their quiescent length, for instance returning to 70 to 100 percent of their quiescent length. The elastic fibers have resiliency to return to their undisturbed state after removal of a dialysis needle, and the woven or knitted pattern further facilitates the self-sealing mechanism by substantially maintaining their pattern during puncture by a dialysis needle thereby allowing the elastic fibers to return to their undisturbed state after removal of the dialysis needle. Furthermore, the woven or knitted pattern by itself also provides resiliency as a dialysis needle moves the fibers in the pattern as it traverses the AV access graft thereby creating a tension or stress within the pattern that acts to move the fibers to their undisturbed state after removal of the dialysis needle.

FIG. 6 depicts a high profile woven portion 36 of velour surface 14 taken along the A—A axis of FIG. 1. Woven portion 36 forms the exterior layer 18 of the graft 10. The woven portion 36 includes interlacing warp yarns 37 and fill yarns 38. Warp yarns 37 are further shown as 37a indicating they are in the top layer of the weave, 37b indicating their presence in the bottom layer of the weave and 37c indicating an overlap over a multitude of fill yarns 38. Warp yarns 37 run in a lengthwise direction in the graft and define the width of the graft. Fill yarns 38 are further shown as top fill yarns 38a and bottom fill yarns 38b. The fill yarns are woven with the warp yarns as shown in FIG. 6. For example, a filling yarn shuttle (not shown) passes across warp yarn 37 while selected warp yarns 37 are lifted according to a specific weaving pattern.

Warp yarn 37c overlays a plurality of fill yarns 38. As shown in FIG. 6, warp yarn 37c is overlaid above seven fill yarns. Warp yarn 37c forms exterior loops, such as loops 30, of the outer surface 32 of flat tubular graft 28. Desirably, warp yarn 37c overlays from 3 to 11 fill yarns to provide an exterior loop that extends outwardly from about 1 mm to about 5 mm after these loops are raised. Furthermore, the location of one raised loop can be varied with respect to the location of another raised loop by selecting different weaving patterns. Twill or satin weaving patterns are among the useful patterns for providing different patterns of exterior loop or velour textures.

Figure 10:
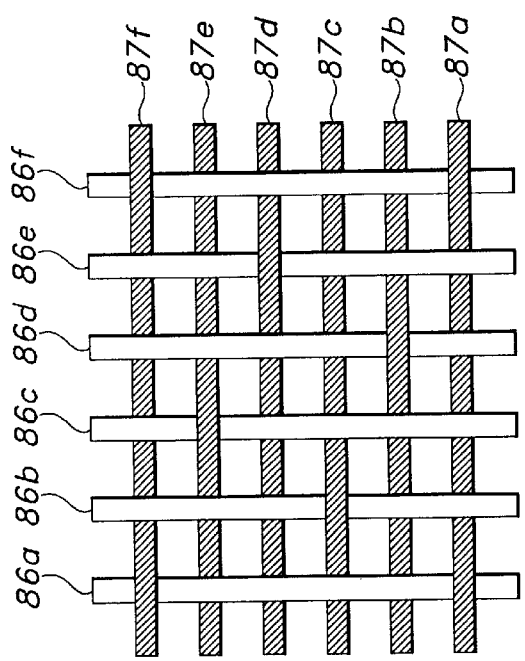
FIG. 10 is an illustration of a satin weave.
Figure 9:
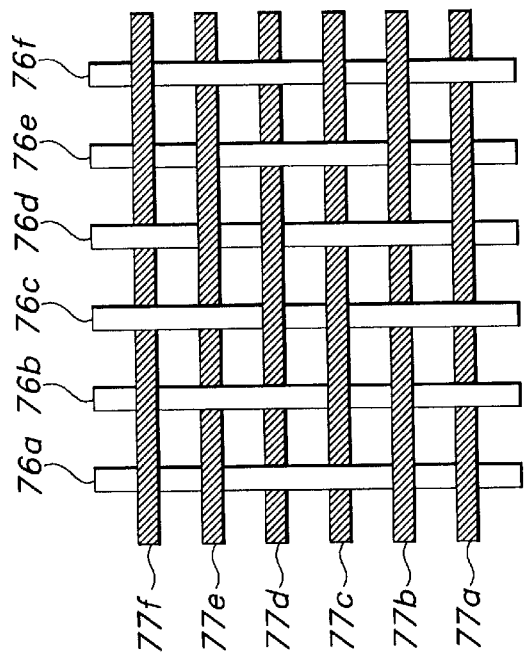
FIG. 9 is an illustration of a twill weave.

FIGS. 9 and 10 illustrate a twill weave 75 and a satin weave 85, respectively. A twill weave has a fill yarn over one or more warp yarns and under one or more warp yarns in a regular succession or pattern. For example, twill weave 75 is depicted in FIG. 9 as a 2/2 twill weave. Fill yarn 77a is under warp yarns 76b and 76c and is over warp yarns 76d and 76e. The next fill yarn, i.e., fill yarn 77b, is under warp yarns 76c and 76d and is over warp yarns 76e and 76f. As a result of the regular succession, raised loops may be formed in a diagonal direction.

FIG. 10 illustrates a satin weave 85, which is depicted as a 4/1 satin weave. A satin weave lacks the distinct diagonal pattern of a twill weave. For example, fill yarn 87a is over warp yarns 86a and 86f and under the remaining warp yarns 86b–86e. The next fill yarn, i.e., fill yarn 87b, is over warp yarn 86d and under the remaining warp yarns 86a–c and 86e–f. The next fill yarn, i.e., fill yarn 87c, is over warp yarn 86b and under the remaining warp yarns 86a and 86c–f. With such a pattern a diagonal pattern of raised loops is not achieved with a satin weave.

The weaving patterns of FIGS. 9 and 10 are for illustration of a twill weave and a satin weave. The patterns depicted in these figures are not intended to limit either the twill weave or the satin weave to a specific pattern, and other patterns of twill and satin weaves are useful with the present invention.

The interior layer 19 of tubular wall 13 may also be a woven fabric pattern. A plain weave 40 is shown in FIG. 7. Warp yarns 42 are interlaced with fill yarns 43 and alternate between a bottom and a top portion. Such an alternating pattern provides interior surface 12 with a smooth surface texture.

The exterior layer 18 and the interior layer 19 are interconnected to form tubular wall 13 of graft 10. In one aspect of the present invention yarns from the woven portion 36 of exterior layer 18 are interwoven with yarns from the plain weave 40 of interior layer 19. For example, as depicted in FIG. 8, warp yarn 39 interconnects the fill yarns 38 other woven portion 36 and the fill yarns 43 of the plain weave 40. Any of the warp or fill yarns may be used to interconnect the two weaves or two layers. The present invention is not limited to interconnecting warp or fill yarns to join the two woven sections and other means may be suitably used. For example, an adhesive layer (not shown) between the two layers may be used to join one layer to the other layer.

Any type of textile yarn can be used as the warp yarns and fill yarns of the present invention. Of particular usefulness in forming the woven prostheses of the present invention are synthetic materials such as synthetic polymers. Synthetic yarns suitable for use in the present invention include, but are not limited to, polyesters, polypropylenes, polyethylenes, polyurethanes and polytetrafluoroethylenes. The yarns may be of the monofilament, multifilament, spun type or combinations thereof.

The yarns used in forming the woven grafts of the present invention may be flat, twisted, textured or combinations thereof. Furthermore, the yarns may have high, low or moderate shrinkage properties or combination of different shrinkage properties. Additionally, the yarn type and yarn denier can be selected to meet specific properties desired for the prosthesis, such as porosity, flexibility and texture of the outer velour surface. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used with the present invention may have a denier from about 20 to about 1000, preferably from about 40 to about 300. Preferably, the warp and fill yarns are polyester, such as polyethylene terapthalate (PET), and most preferably the warp and fill yarns are one ply, 50 denier, 48 filament flat and texturized polyester.

The graft of the present invention can be woven using any known weave pattern in the art, including, plain weaves, basket weaves, satin weaves, twill weaves and the like, and is preferably woven using a plain, a satin or a twill pattern. Desirably, the weave patterns have about 25–260 warp yarns (ends) per inch per layer and about 20–90 fill yarns (picks) per inch per layer. The relaxed wall thickness of the graft should be greater than a conventionally useful thickness, but is preferably no greater than about 10.0 mm, with the more preferable wall thickness being from about 3.0 mm to about 7.0 mm. Upon compression the compressed thickness will be smaller than relaxed wall thickness.

As noted above, preferably the tubular-woven graft of the present invention is constructed of polyester which is capable of shrinking during a heat-set process. For instance, such grafts are typically flat-woven in a tubular form. Due to the nature of the flat-weaving or flat-knitting process, the tubular graft is generally flat in shape after weaving or knitting. Such grafts, however, when constructed of shrinkable polyester yarn, can be heat set on a mandrel to form a generally circular shape.

Such a heat-setting process is accomplished by first weaving the graft in a seamless tubular form out of a material capable of shrinking during a heat-setting or similar process. The graft may be preshrunk before it is placed on a mandrel. Preshrinking may be achieved by submitting the woven graft to moderate temperatures, such as 190° F. to 400° F. Usually the graft is placed in a medium for the preshrinking. Such a medium can include without limitation hot water, a chemical fluid, such as methylene chloride, or a gas, such as air or carbon dioxide. The graft of the present invention, however, may suitably be made without such a preshrinking of the yarns.

After the graft is woven or alternatively woven and preshrunk, the graft is placed on a mandrel, and heated in an oven at a temperature and time capable of causing the yarns of the graft to heat set to the shape and diameter of the mandrel. Preferably polyester yarns are used as the warp and fill yarns, and the heat setting is accomplished at time and temperatures appropriate for the material. For example, heat setting can be accomplished at about 190–400° F. for a period of about less than an hour. Temperatures in the range of 190° F.–300° F. are also useful. Desirably, temperatures from about 190° F. to about 260° F. are also useful. Desirably, time periods from about 5 to about 30 minutes are useful. More desirably, with time periods from about 10 to about 20 minutes are useful Other methods of heat setting known in the art may be employed. After such a heat setting process, the graft can be formed into a shape desired for implantation, having a generally circular inner lumen.

The heat-setting process also raises the loops outwardly from the outer surface of the graft when there is a difference in shrinkage properties of the yarns used in the different woven layers. Desirably, at least some of the yarns of the inner woven layer should have exhibit greater shrinkage upon heat setting as compared to at least some of the yarns of the outer woven layer. The loops can also be raised, in part, by mechanically raising the loops, such as compressing the graft longitudinally to raise the loops, and then heat setting the graft to secure the raised loop orientation.

In another aspect of the present invention, graft 10 is a knitted fabric graft that includes a top knitted layer 50 for exterior layer 18 and a bottom knitted layer 60 or 65 for interior layer 19. The top knitted layer 50 is depicted in FIG. 11 from the A—A perspective of velour surface 14 of graft 10. Top knitted layer 50 is depicted as a sharkskin pattern to form the top layer of graft 10. Top knitted layer 50 is a warp knitted structure having a trellis yarn 51 and a velour yarn 55, interrelated as shown. Velour yarn 55 overlays the trellis yarn 51 to form the velour texture of the outer surface 14 of the present invention. Desirably, the velour yarn 55 overlays from about 3 to about 9 trellis loops 53 to form raised loops 16 of graft 10. In one aspect of the present invention the velour yarn 55 overlays about 7 trellis loops 53.

The bottom knitted layer 60 is depicted as a tricot pattern in FIG. 12. This bottom knitted layer 60 has a trellis yarn 61 and a pile yarn 63 to form the smooth interior surface of inner surface 12. Interior layer 19 may be knitted either in a tricot pattern, which is depicted in FIG. 12, or in a locknit pattern, which is depicted in FIG. 13. The locknit pattern 65 also has a trellis yarn 67 and a pile yarn 69 that forms the smooth interior surface of inner surface 12. Trellis loops 62 and 68 provide integrity for the respective tricot pattern 60 and locknit pattern 65.

Figure 14:
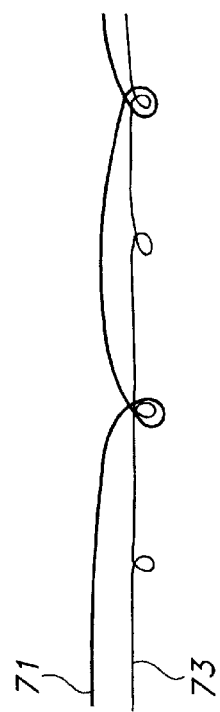
FIG. 14 is a partial cross-sectional view of knitting patterns having interlacing yarns between the exterior and interior portions of the graft wall.

As depicted in FIG. 14, some of the yarns 71 from the top knitted layer 50 are interlaced with yarns 73 of the bottom knitted layer 60 or 65 to interlace interior layer 19 and exterior layer 18 of tubular wall 13 of graft 10.

Any type of textile product can be used as yarns for the knitted textile graft of the present invention. Of particular usefulness in forming the knitted fabric prosthesis of the present invention are synthetic materials such as synthetic polymers. Synthetic yarns suitable for use in the present invention include, but are not limited to, polyesters, including PET polyesters, polypropylenes, polyethylenes, polyurethanes and polytetrafluoroethylenes. The yarns may be of the monofilament, multifilament, spun type or combinations thereof. The yarns may also be flat, twisted or textured, and may have high, low or moderate shrinkage properties or combinations thereof.

The knitted textile graft of the present invention is desirably made on a warp-knitting machine (not shown) using a double needle bar. A useful number of needles per inch for warp knitting is from about 18 to about 36. About 28 needles per inch are particularly suitable. The trellis of the graft is usually made from a yarn having count from 30 to 300 denier. Desirably, the range of yarn counts for the trellis is from about 30 to about 70. A particularly suitable yarn count is about 40 denier. The trellis yarn may be a single ply, a double ply or a multi-ply. The term "multi-ply" is used herein to indicate more than two-ply.

In a typical method of warp knitting the trellis, yarn is fed from two inside beams, each beam being a spool holding a plurality of ends. Two outside beams may be used in conjunction with the inside beams, the outside beams being used for making the loops. Each outside beam also has a plurality of ends. It should be noted, however, that the inside beams may be used for making the loops and the outside beams used for making the trellis. Regardless of which beams are used for the trellis and which for the loops, non-texturized flat yarn is generally used for the trellis and texturized yarn is generally used for the loops. In general, the yarn count for the loops should be at least as great as that of the trellis yarn count. The minimum number of beams used in making the textile graft of the present invention is 2. A greater number of beams, however, may be found useful for specific applications.

The raised loops are made of single-ply multifilament yarn, double-ply yarn or multi-ply yarns. Desirably, multi-ply yarns are used for the loops. The yarn count for making the loops should be between about 30 and about 300 denier, with a desirable range being about 30 to about 70 denier. A particularly suitable yarn count for the loops is about 40 denier.

The extent to which the loops project from the trellis is established when the relative feed rates of the loop and trellis yarns are selected and the ratio of the extents to which the loops protrude outwardly from the trellis is established. In order that the loops may project outwardly from the trellis, the yarn from the beams providing the loop yarn is fed at a higher rate than that for the trellis. The ratio of the rates lies in the range from about 1.25:1 to about 4.50:1. Such rates produce a graft having a ratio of the loop yarn length to trellis yarn length lying between 1.25 and 4.50. Yarns with different shrinkage properties may also be used to control the extent of the loops. For example, the interior knitted layer may contain yarns with a higher shrinkage property as compared to the shrinkage property of the yarns in the exterior knitted layer.

Subsequent to knitting, the fabric is desirably subjected to compacting and heat-setting, as described above, in order to control the porosity of the textile graft and to raise the loops outwardly from the graft surface to form a raised loop or velour textile.

In another aspect of the present invention the high profile AV access graft may be used to provide a method for permitting immediate access to an artery to vein bypass. A method for providing such immediate access includes providing a high profile AV access graft, subcutaneously implanting or tunneling the AV graft into a position between the artery and the vein and securably attaching, for example by suturing, one end of said AV graft to the artery and the other end to the vein. The raised exterior loops of the AV graft form an interspatial volume above the exterior surface of the AV graft in conformability with an intervascular region proximal thereto. During the implantation or tunneling of the AV graft voids in the hypodermic region are created as the AV graft is positioned between the artery and the vein. The raised exterior loops fill any voids resulting from the placement of the AV graft, and as a result the AV graft may be accessed prior to tissue ingrowth or stabilization.

The following examples serve to provide further appreciation of the invention but are not meant in any way to restrict the effective scope of the invention.

EXAMPLES

Example 1

2 Ply Solid Woven Graft With External Velour

The following specifications are used to fabricate a solid woven prosthesis of the present invention.

Weave—2 Ply Solid Woven, Tubular with 7 filling floats on outer ply

Warp Yarn: Textured 50 denier/ 48 filament polyester

Fill Yarn: One ply/textured 50 denier/ 48 filament polyester

Ends per inch: 200

Picks per inch: 60

Subsequent to weaving the graft, the material is scoured in a basic solution of warm water (e.g., 150° F.) and cleaning detergent. It is then rinsed to remove the cleaning agents. Next, the prosthesis is heat-set on mandrels of the final desired inside diameter. Typically, the outside diameter of the mandrel is equal to the diameter of the final prosthesis. The woven tubing is woven to be 5–15% oversize so that it can be mounted onto a mandrel and shrink fitted to an exact diameter.

Heat setting can take place in a steam-heated autoclave at about 250° F. for about 5–10 minutes or in a convection oven at 250° F. –400° F. for about 10–30 minutes. The heat setting can be done in a two-step process. The first step involves heat-setting the prosthesis in its fully extended state to shrink fit the prosthesis snugly to the mandrel. The second heat-setting step entails compressing the prosthesis longitudinally. The compression is on the order of 25–50%. The prosthesis is then heat-set a second time using similar conditions as in the first heat-setting cycle.

As a result of the heat setting, the warp yarns buckle and crimp. The heat locks the yarns in this geometry to build in "spring like" properties. The warp yarns in the outer ply which are floating over 7 picks, would raise from the fabric, forming a filamentous velour surface.

The warp yarns raised from the outer ply are in the form of raised loops after heat setting. The length of the loops extending from the outer ply is varied from about 1 mm to about 5 mm in length.

Example 2

2 Ply Solid Knitted Graft With External Velour

The following specifications are used to fabricate a solid knitted prosthesis of the present invention.

Front Guide Bar: 4–5/1–0

Back Guide Bar: 1–0/4–5

Feed Ratio: 3:1

Shrinkage of yarn on Back bar: <20%

Shrinkage of yarn on Front bar: >5%

Yarn Type:
  Front Bar: Stretch textured 40 denier polyester multifilament yarn.
  Back Bar: 40 denier flat yarn or 40 denier textured high shrinkage multifilament polyester yarn.

Subsequent to knitting, the prosthesis is heat set as in Example 1 to form a filamentous velour surface. The length of the loops extending from the outer surface is varied from about 1 mm to about 5 mm in length.

The invention being thus described, it will now be evident to those skilled in the art that the same may be varied in many ways. Such variations are not to be regarded as a departure from the spirit and scope of the invention, and all such modifications are intended to be included within the scope of the following claims.

What is claimed is:

1. A synthetic fabric tubular vascular graft comprising:
   a first tubular fabric layer having a pattern of yarns interlaced to form a smooth inner surface and an opposed outer surface; and
   a second tubular fabric layer having a pattern of yarns different from said pattern in said first layer interlaced to form an exterior surface and having filaments of yarns raised in loops above said exterior surface to form a raised or velour texture, wherein said loops extend from about 1 mm to about 5 mm in length from said exterior surface and further wherein at least one yarn from said first fabric layer is interlaced with yarns of said second fabric layer to secure said second fabric layer to first fabric layer and further wherein said yarns include warp and fill yarns woven to form said first and said second fabric layers, provided that said warp and said fill yarns of said first fabric layer are woven in a plain pattern and said warp and said fill yarns of said second fabric layer are woven in a twill or a satin pattern.

2. The graft of claim 1 wherein said yarns of said first and said second layers have a fluid-tight quiescent state and further wherein said yarns are elastic synthetic fibers capable of returnably moving from a punctured altered state to the quiescent state to provide a self-sealing mechanism thereat.

3. The graft of claim 1 wherein the pattern of said first layer and the pattern of said second layer have a fluid-tight quiescent state and further wherein the patterns have resiliency capable of returnably moving from a punctured altered state to the quiescent state to provide a self-sealing mechanism thereat.

4. The graft of claim 1 wherein said raised external loops have a resiliency to provide a self-sealing mechanism after puncture of said graft.

5. The graft of claim 1 wherein said loops are warp yarns and each of said warp yarns of said loops overlay from 5 to 9 fill yarns.

6. The graft of claim 1 wherein said yarns are selected from the group consisting of monofilament yarns, multifilament yearns, spun type yarns, flat yarns, twisted yarns, textured yarns, and combinations thereof.

7. The graft of claim 1 wherein said yarns are selected from the group of materials selected from polyesters, polypropylenes, polyethylenes, polyurethanes, polytetrafluoroethylenes or combinations thereof.

8. The graft of claim 7 wherein said polyesters include polyethylene terephthalate polyesters.

9. The graft of claim 1 wherein said yarns are single ply or multiply yarns.

10. The graft of claim 1 wherein said yarns of said first fabric layer have a first heat shrinkable property upon heat setting, and said yarns of said second fabric layer have a second heat shrinkable properly upon heat setting, and further wherein said second heat shrinkable property is greater than said first heat shrinkable property.

11. The graft of claim 1 wherein said graft is an arteriovenous access graft.

12. The graft of claim 11 wherein said arteriovenous access graft is stabilized for access within one week or less after implantation.

13. The graft of claim 1 wherein said loops form an interspatial volume in conformability with intervascular region proximal thereto to permit access to said graft prior to stabilization of said graft.

14. A synthetic fabric tubular vascular graft comprising:
a first tubular fabric layer having a pattern of yarns interlaced to form a smooth inner surface and an opposed outer surface; and
a second tubular fabric layer having a pattern of yarns different from said pattern in said first layer interlaced to form an exterior surface and having filaments of yarns raised in loops above said exterior surface to form a raised or velour texture, wherein said loops extend from about 1 mm to about 5 mm in length from said exterior surface and further wherein at least one yarn from said first fabric layer is interlaced with yarns of said second fabric layer to secure said second fabric layer to first fabric layer and further wherein said yarns include pile yarns, trellis yarns and velour yarns, and further wherein said pile yarns and said trellis yarns are knitted to form said first fabric layer and said velour yarns and said trellis yarns are knitted to form said second fabric layer, provided that said pile yarns and said trellis yarns of said first fabric layer are knitted in a tricot or locknit pattern, and provided that said velour yarns and said trellis yarns of said second fabric layer are knitted in a sharkskin pattern.

15. The graft of claim 13 wherein said yarns of said first and said second layers have a fluid-tight quiescent state and further wherein said yarns are elastic synthetic fibers capable of returnably moving from a punctured altered state to the quiescent state to provide a self-sealing mechanism thereat.

16. The graft of claim 13 wherein the pattern of said first layer and the pattern of said second layer have a fluid-tight quiescent state and further wherein the patterns have resiliency capable of returnably moving from a punctured altered state to the quiescent state to provide a self-sealing mechanism thereat.

17. The graft of claim 13 wherein said raised external loops have a resiliency to provide a self-sealing mechanism after puncture of said graft.

18. The graft of claim 13 wherein said loops are said velour yarns, and further wherein each of said velour yarns forming said loops overlay from 5 to 9 trellis yarns.

19. The graft of claim 14 wherein said yarns are selected from the group consisting of monofilament yarns, multifilament yearns, spun type yarns, flat yarns, twisted yarns, textured yarns, and combinations thereof.

20. The graft of claim 14 wherein said yarns are selected from the group of materials selected from polyesters, polypropylenes, polyethylenes, polyurethanes, polytetrafluoroethylenes or combinations thereof.

21. The graft of claim 20 wherein said polyesters include polyethylene terephthalate polyesters.

22. The graft of claim 14 wherein said yarns are single ply or multi-ply yarns.

23. The graft of claim 14 wherein said yarns of said first fabric layer have a first heat shrinkable property upon heat setting, and said yarns of said second fabric layer have a second heat shrinkable properly upon heat setting, and further wherein said second heat shrinkable property is greater than said first heat shrinkable property.

24. The graft of claim 14 wherein said graft is an arteriovenous access graft.

25. The graft of claim 24 wherein said arteriovenous access graft is stabilized for access within one week or less after implantation.

26. The graft of claim 14 wherein said loops form an interspatial volume in conformability with intervascular region proximal thereto to permit access to said graft prior to stabilization of said graft.

* * * * *

UNITED STATES PATENT AND TRADEMARK OFFICE
CERTIFICATE OF CORRECTION

PATENT NO. : 6,547,820 B1
DATED : April 15, 2003
INVENTOR(S) : Staudenmeier, M.

It is certified that error appears in the above-identified patent and that said Letters Patent is hereby corrected as shown below:

<u>Column 4,</u>
Line 56, should read -- ...before it can be used for... --.

<u>Column 6,</u>
Line 16, should read -- ...yarns 38 of the woven... --.

<u>Column 10,</u>
Line 13, should read -- Shrinkage of yarn on Back bar: >20% --.
Line 14, should read -- Shrinkage of yarn on Front bar: <5% --.

<u>Column 11,</u>
Line 3, should read -- ...multifilament yarns,... --.

<u>Column 12,</u>
Line 3, should read -- ...the graft of claim 14 wherein... --.
Line 8, should read -- ...the graft of claim 14 wherein... --.
Line 14, should read -- ...the graft of claim 14 wherein... --.
Line 18, should read -- ...the graft of claim 14 wherein... --.
Line 22, should read -- ...multifilament yarns, ... --.

Signed and Sealed this

Twenty-third Day of December, 2003

JAMES E. ROGAN
*Director of the United States Patent and Trademark Office*